United States Patent [19]

Takahashi

[11] Patent Number: 5,027,791
[45] Date of Patent: Jul. 2, 1991

[54] AIR AND WATER SUPPLY APPARATUS FOR ENDOSCOPE

[75] Inventor: Nagashige Takahashi, Tokyo, Japan

[73] Assignee: Asahi Kogaku Kogyo Kabushiki Kaisha, Tokyo, Japan

[21] Appl. No.: 452,390

[22] Filed: Dec. 19, 1989

[30] Foreign Application Priority Data

Dec. 22, 1988 [JP] Japan ................................. 63-324635
Dec. 22, 1988 [JP] Japan ................................. 63-324636

[51] Int. Cl.⁵ ............................................. A61B 1/00
[52] U.S. Cl. .......................................................... 128/4
[58] Field of Search ........................................ 128/4, 6

[56] References Cited

U.S. PATENT DOCUMENTS

| | | | |
|---|---|---|---|
| 4,261,343 | 4/1981 | Ouchi et al. | 128/4 |
| 4,325,362 | 4/1982 | Ouchi et al. | 128/4 |
| 4,509,507 | 4/1985 | Yabe | 128/4 A |
| 4,537,209 | 8/1985 | Sasa | 128/4 A |
| 4,552,130 | 11/1985 | Kinoshita | 128/4 A |
| 4,676,242 | 6/1987 | Doi | 128/398 X |

*Primary Examiner*—William H. Grieb
*Attorney, Agent, or Firm*—Sandler, Greenblum & Bernstein

[57] ABSTRACT

An air and water supply apparatus for an endoscope having an elongated insert part and a control part connected to the proximal end of the insert part, comprising a cylinder provided in the control part, a pair of first air and water tubes for supplying air and water, respectively, into the cylinder, a pair of second air and water tubes for sending air and water, respectively, to the distal end of the insert part from the cylinder, a water supply switching valve slidably fitted in the cylinder to change the condition of communication between the first and second water tubes, and an air supply switching valve slidably fitted in the water supply switching valve to change the condition of communication between the first and second air tubes, whereby the first air tube and the second water tube are communicated with each other by pushing both the water and air supply switching valves into the cylinder or by pulling the air supply switching valve in the direction in which it is drawn out of the cylinder. Thus, air is sent into the second water tube from the first air tube to purge the water remaining in the second water tube.

15 Claims, 5 Drawing Sheets

AIR AND WATER SUPPLY APPARATUS FOR ENDOSCOPE

BACKGROUND OF THE INVENTION

1. Field of the Invention

The present invention relates to an air and water supply apparatus for an endoscope which is designed so that air and water can be selectively sprayed from the distal end of the insert part of the endoscope.

2. Description of the Related Art

Endoscopes are generally designed to be capable of spraying water from a nozzle through a water tube to wash dirt off the surface of a viewing window provided at the distal end of the insert part. Since bacteria or viruses in the patient's body cavity are likely to invade the water remaining in the water tube, if the endoscope having been used for one patient is used for another with the remaining water left as it is, bacteria or viruses may be transmitted to the second patient. Accordingly, the remaining water must always be purged from the water tube after the endoscope has been used.

One typical example of conventional water purging systems has heretofore been arranged such that a switching valve is provided in a water tank for storing water to be supplied for washing and, with this switching valve switched to the position for purging, a water supply operation is conducted on the endoscope side to supply air into the water tube, thereby purging the remaining water from the water tube.

The above-described system suffers, however, from the following problems. The water tank is generally attached to a light source device or other associated device and therefore disposed away from the control part of the endoscope. Accordingly, the purging operation is commonly conducted when the endoscope is washed after being removed from the patient's body cavity since it is exceedingly difficult to carry out the purging operation with the endoscope being inserted in the patient's body cavity. However, as air for purging is supplied into the water tube, the water remaining in the water tube gushes out of the nozzle and scatters in the form of spray at the end of the purging operation. Therefore, if the water has been contaminated by bacteria or viruses, the purging operation may cause these bacteria or viruses to scatter in the room, which may invite in-hospital infection.

Thus far, substantially no attention has been paid to this phenomenon and therefore no measures have been taken to solve the problem. The present inventor, however, noticed the seriousness of this problem and came to invent the air and water supply apparatus for an endoscope of this application with a view to solving the problem.

SUMMARY OF THE INVENTION

An object of the present invention is to provide an air and water supply apparatus for an endoscope which is designed so that the water remaining in the water tube can be readily purged with a simple apparatus, without the fear of in-hospital infection.

Other objects and advantages of the present invention will become apparent from the following detailed description of illustrated embodiments of the invention.

According to the present invention, there is provided an air and water supply apparatus for an endoscope having an elongated insert part and a control part connected to the proximal end of the insert part, comprising: a cylinder provided in the control part; a pair of first air and water tubes for supplying air and water, respectively, into the cylinder; a pair of second air and water tubes for sending air and water, respectively, to the distal end of the insert part from the cylinder; a water supply switching valve slidably provided in the cylinder to change the condition of communication between the first and second water tubes; and an air supply switching valve provided in the cylinder so as to be slidable in the same direction as the direction of slide of the water supply switching valve to change the condition of communication between the first and second air tubes, whereby in a stand-by state the first and second air and water tubes are cut off from each other by the air and water supply switching valves; when the air supply switching valve is pushed into the cylinder, the first and second air tubes are communicated with each other; when the water supply switching valve is pushed into the cylinder, together with the air supply switching valve, the first and second air tubes are cut off from each other, while the first and second water tubes are communicated with each other; and when both the water and air supply switching valves are further pushed into the cylinder, the first air tube and the second water tube are communicated with each other.

In addition, there is provided an air and water supply apparatus for an endoscope having an elongated insert part and a control part connected to the proximal end of the insert part, comprising: a cylinder provided in the control part; a pair of first air and water tubes for supplying air and water, respectively, into the cylinder; a pair of second air and water tubes for sending air and water, respectively, to the distal end of the insert part from the cylinder; a water supply switching valve slidably provided in the cylinder to change the condition of communication between the first and second water tubes; and an air supply switching valve provided in the cylinder so as to be slidable in the same direction as the direction of slide of the water supply switching valve to change the condition of communication between the first and second air tubes, whereby in a stand-by state the first and second air and water tubes are cut off from each other by the air and water supply switching valves; when the air supply switching valve is pushed into the cylinder, the first and second air tubes are communicated with each other; when the water supply switching valve is pushed into the cylinder, together with the air supply switching valve, the first and second air tubes are cut off from each other, while the first and second water tubes are communicated with each other; and when the air supply switching valve which is in the stand-by state is pulled in the direction in which it is drawn out of the cylinder, the first air tube and the second water tube are communicated with each other.

In addition, there is provided an air and water supply apparatus for an endoscope having an elongated insert part and a control part connected to the proximal end of the insert part, comprising: a cylinder provided in the control part; a pair of first air and water tubes for supplying air and water, respectively, into the cylinder; a pair of second air and water tubes for sending air and water, respectively, to the distal end of the insert part from the cylinder; and a valve device provided in the cylinder, the valve device being capable of changing over at least the following two states from one to the other, that is, a state wherein the first and second water tubes are communicated with each other and a state wherein the first air tube and the second water tube are communicated with each other.

BRIEF DESCRIPTION OF THE DRAWINGS

The present invention may be more fully understood from the description of preferred embodiments of the invention set forth below, together with the accompanying drawings, in which.

DESCRIPTION OF THE EMBODIMENTS

Figure 5:
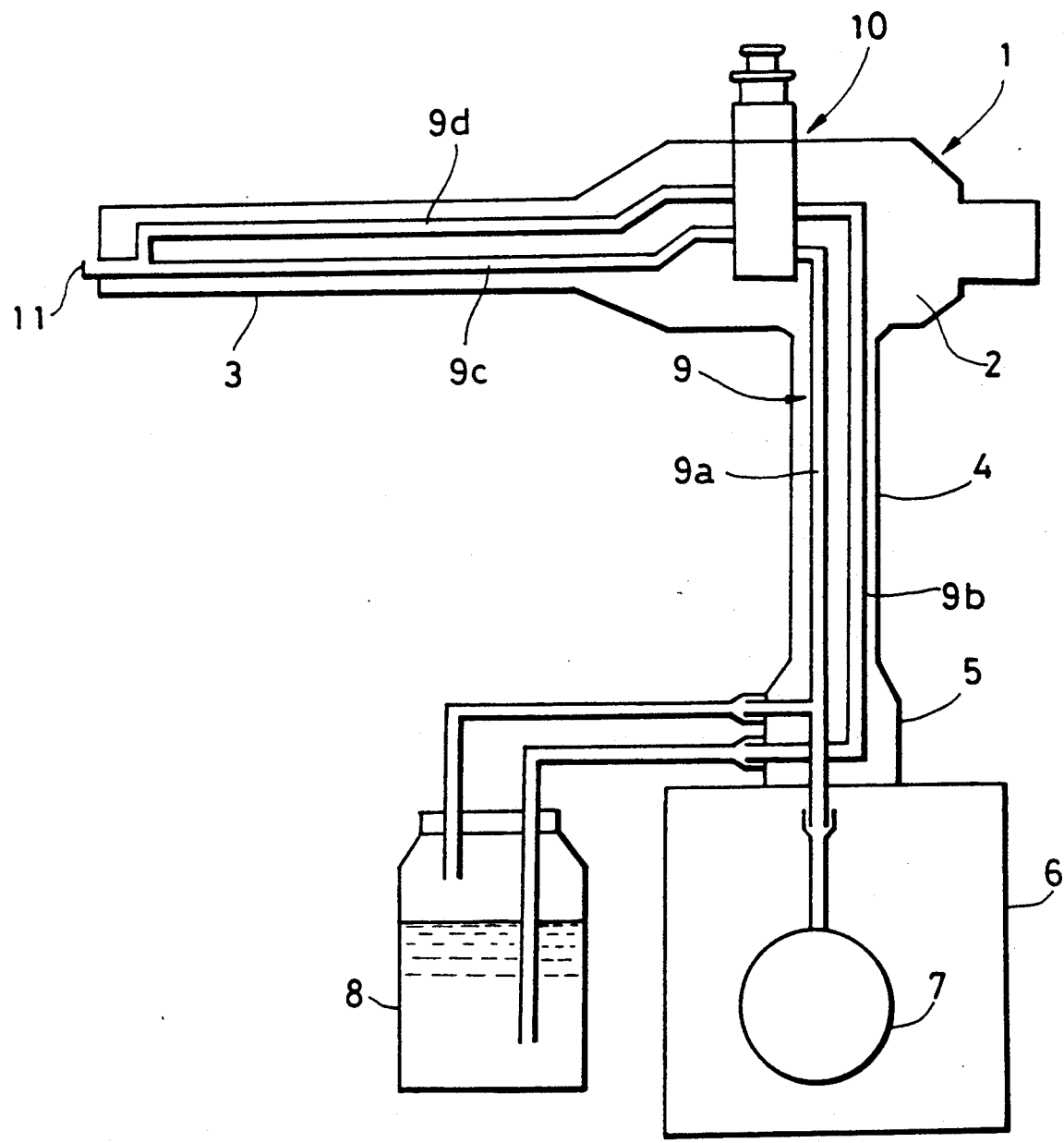
FIG. 5 shows the whole pipeline arrangement of the air and water supply system in the present invention.

Referring first to FIG. 5, which shows the whole pipeline arrangement of the air and water supply system in the present invention, the reference numeral 1 denotes an endoscope which comprises a control part 2, an elongated insert part 3 connected at the proximal end thereof to the control part 2 and a flexible connecting tube 4 which is also connected to the control part 2. The insert part 3 is flexible and designed to be inserted into a hollow organ of the patient's body. A connector 5 is provided at the distal end of the flexible connecting tube 4. The connector 5 is capable of being detachably connected to an air pump 7 provided inside a light source device 6. The reference numeral 8 denotes a water tank which is capable of delivering water stored therein by means of the pressure applied from the air pump 7.

An air and water supply pipeline 9 is provided inside the endoscope 1, and a switching valve device 10, which is provided in the control part 2, is interposed in the intermediate portion of the air and water supply pipeline 9. The reference numerals 9a and 9b respectively denote an air tube for supplying air to the switching valve device 10 and a water tube for supplying water to it. The air tube 9a is connected to the air pump 7, while the water tube 9b is connected to a tube which opens in the water stored in the water tank 8. The reference numerals 9c and 9d respectively denote an air tube for sending out the air from the switching valve device 10 and a water tube for sending out water from the switching valve device 10. These air and water tubes 9c and 9d are mutually connected to a single nozzle 11 at the distal end of the insert part 3. The nozzle 11 opens to the surface of an objective lens (not shown). It should be noted that the nozzle can be individually provided for each of the air and water tubes 9c and 9d.

Figure 1:
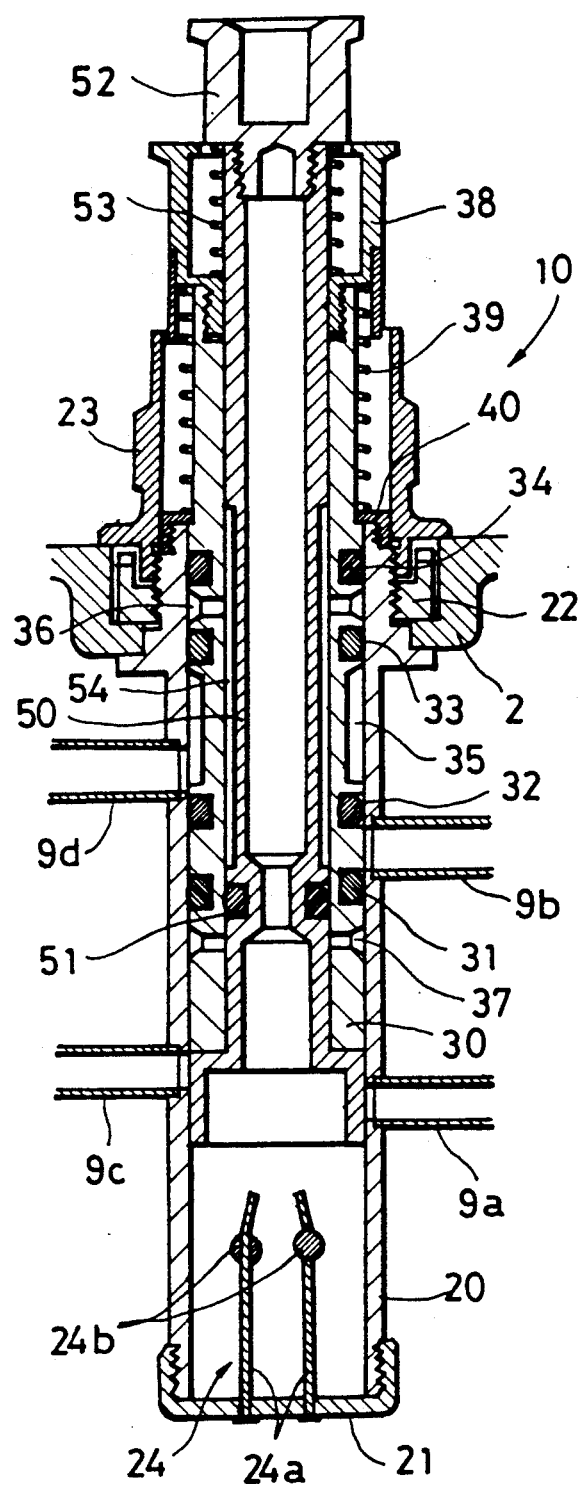
FIG. 1 is a sectional view of a first embodiment of the present invention in a stand-by state.

FIG. 1 shows the switching valve device 10 in the first embodiment of the present invention. In the figure, the reference numeral 20 denotes a cylinder. The air tube 9a, the water tube 9b, the air tube 9c and the water tube 9d are connected to respective portions of the side wall of the cylinder 20. The bottom of the cylinder 20 is hermetically closed with a cap 21. The reference numeral 22 denotes a nut used to secure the cylinder 20 to the control part 2. The reference numeral 23 denotes a cylindrical cover member which surrounds the top portion of the cylinder 20.

The cap 21 attached to the bottom of the cylinder 20 is provided with an intermediate stopper 24 for stopping air and water supply switching valve bodies 50 and 30 in the position for supplying water when these valve bodies are pushed into the cylinder 20. The intermediate stopper 24 comprises, for example, a pair of resilient rod members (or plate members) each of which is rigidly secured at one end thereof (the lower end as viewed in the figure) to the cap 21 and bent slightly inward at the upper part thereof and stainless steel balls 24b rigidly secured to the bent portions or their vicinities, respectively.

Inside the cylinder 20 are provided a water supply switching valve body 30 for changing the condition of communication between the water tubes 9b and 9d and an air supply switching valve body 50 for changing the condition of communication between the air tubes 9a and 9c in such a manner that the two valve bodies 30 and 50 are slidable in the axial direction. The water supply switching valve body 30 is a cylindrical valve body which is fitted in the cylinder 20. The water supply switching valve body 30 has first to fourth O-rings 31, 32, 33 and 34 fitted on the outer peripheral surface thereof. In a stand-by state, the first and second O-rings 31 and 32 seal the opening of the water tube 9b from both sides thereof, and the second and third O-rings 32 and 33 seal the opening of the water tube 9d from both sides thereof. Between the second and third O-rings 32 and 33 is formed a communicating groove 35 for water which provides communication between the water tubes 9b and 9d when the apparatus is in a water supply state. Between the third and fourth O-rings 33 and 34 is provided a communicating hole 36 for purging which serves as an air flow path when the apparatus is in a water purging state, and another communicating hole 37 for purging is provided at the inner side (the lower side as viewed in the figure) of the first O-ring 31.

The upper end (as viewed in the figure) of the water supply switching valve body 30 projects from the upper end of the cylinder 20. A water control button 38 is screwed onto the projecting end portion of the valve body 30. The water supply switching valve body 30 and the water control button 38 constitute in combination a water supply switching valve. The water supply switching valve body 30 is constantly biased in the direction in which it springs out of the cylinder 20 by a first coil spring 39 having relatively strong spring force. The reference numeral 40 denotes a stopper which prevents the water supply switching valve body 30 from springing out of the cylinder 20.

The air supply switching valve body 50 is slidably fitted in the water supply switching valve body 30, and an O-ring 51 for sealing is fitted on the fitting portion of the valve body 50. The lower end portion of the air supply switching valve body 50 is fitted to the inner wall of the cylinder 20 to close the respective openings of the air tubes 9a and 9c. The upper end of the air supply switching valve body 50 projects from the upper end of the water supply switching valve body 30. An air control button 52 is screwed onto the projecting end portion of the air supply switching valve body 50, the air control button 52 projecting beyond the upper end of the water control button 38. The air supply switching valve body 50 and the air control button 52 constitute in combination an air supply switching valve. The reference numeral 53 denotes a second coil spring which biases the air supply switching valve body 50 in the direction in which it springs out of the water supply switching valve body 30, the second coil spring 53 being weaker than the first coil spring 39. It should be noted that the air supply switching valve body 50 in this embodiment is not provided with a leak hole for constantly leaking to the atmosphere the air sent into the cylinder 20 from the air tube 9a and it is hermetically closed with the air control button 52. Moreover, the air tube 9a is closed with the lower end portion of the air supply switching valve body 50. Therefore, there is no possibility that contaminative matter, for example, mucus or blood, in the patient's body cavity will flow backward into the cylinder 20 through the air tube 9c and there is no fear of such contaminative matter being scattered outside.

The reference numeral 54 denotes a communicating groove for purging which is formed in the outer periphery of the air supply switching valve body 50 so that the air in the air tube 9a will pass therethrough when the apparatus is in a water purging state.

The operation of the above-described embodiment will next be explained.

FIG. 1 shows the apparatus which is in a stand-by state. In this state, the air tubes 9a and 9c are cut off from each other by the air supply switching valve body 50, while the water tubes 9b and 9d are cut off from each other by the water supply switching valve body 30. Accordingly, neither air nor water is supplied.

Figure 2:
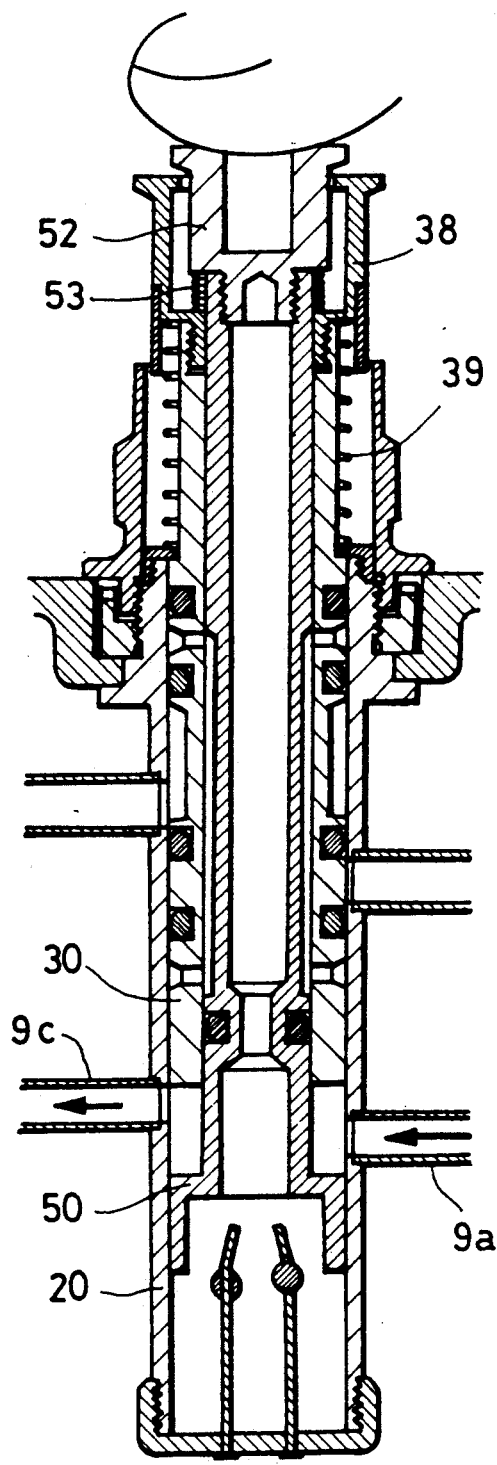
FIG. 2 is a sectional view of the first embodiment of the present invention in an air supply state.

When the air control button 52 is pressed down by a fingertip, as shown in FIG. 2, since the first coil spring 39 is stronger than the second coil spring 53, the water control button 38 is not pushed down, and the air control button 52 is alone pushed down. In consequence, the air supply switching valve body 50 is pushed into the water supply switching valve body 30 and the cylinder 20. As a result, the air tubes 9a and 9c are communicated with each other and the air in the air tube 9a is sent into the air tube 9c via the cylinder 20, thus the apparatus entering into an air supply state.

Figure 3:
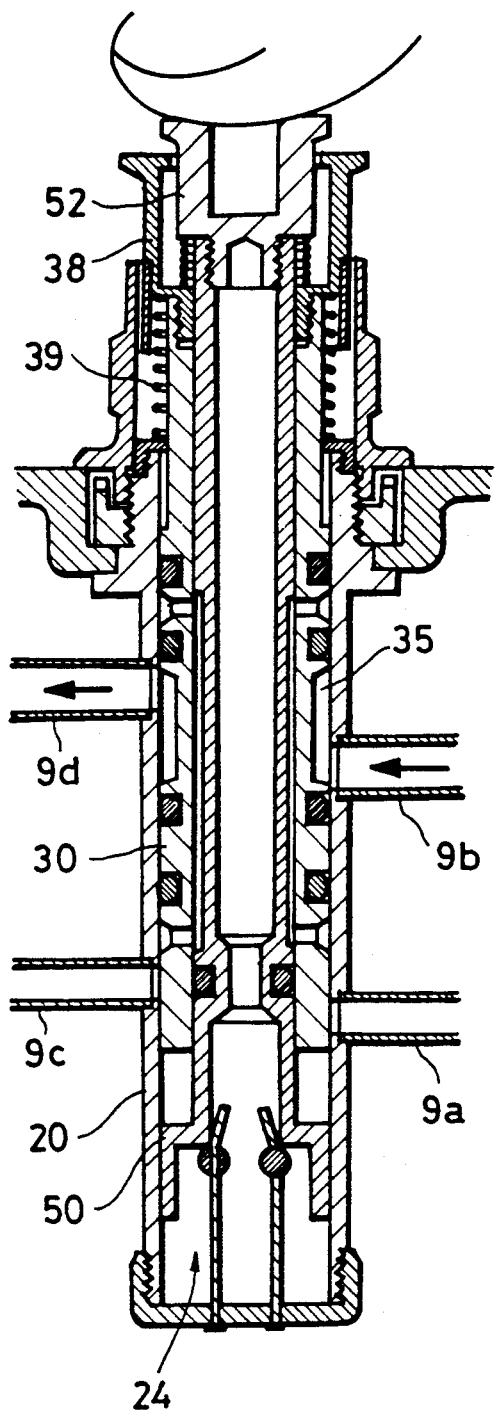
FIG. 3 is a sectional view of the first embodiment of the present invention in a water supply state.

As the air control button 52 is further pressed down by increasing the pressure thereon, as shown in FIG. 3, the first coil spring 39 is compressed and consequently the water control button 38 is pushed into the cylinder 20, together with the air control button 52. In consequence, the water supply switching valve body 30 is pushed into the cylinder 20 until the bottom of the air supply switching valve body 50 abuts against the intermediate stopper 24. As a result, the air tubes 9a and 9c are cut off from each other by the water supply switching valve body 30. On the other hand, the water tubes 9b and 9d are communicated with each other through the communicating groove 35 for water, so that the water in the water tube 9b is sent into the water tube 9d, thus the apparatus enters into a water supply state.

Figure 4:
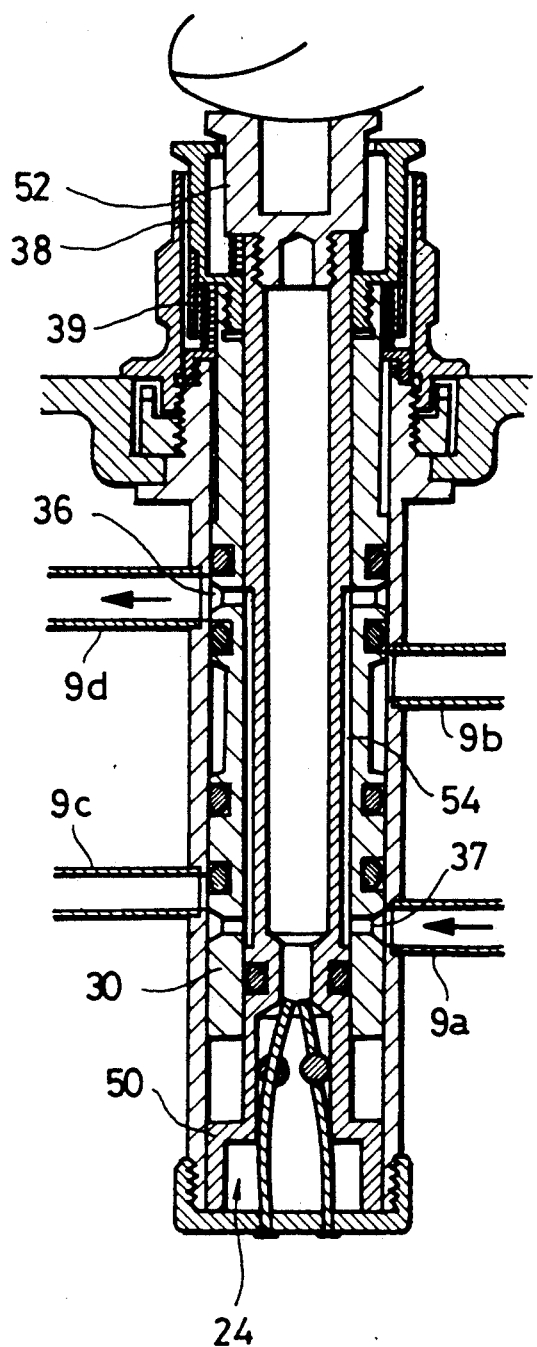
FIG. 4 is a sectional view of the first embodiment of the present invention in a state wherein the water remaining in the water tube is being purged.

As the control buttons 52 and 38 are pressed even more strongly, as shown in FIG. 4, the intermediate stopper 24 is pushed and bent inward by the bottom of the air supply switching valve body 50, thus allowing the air and water supply switching valve bodies 50 and 30 to be further pushed into the cylinder 20. In consequence, the respective openings of the water and air tubes 9b and 9c are closed by the water supply switching valve body 30, while the air and water tubes 9a and 9d are communicated with each other through the purging communicating holes 36, 37 and the purging communicating groove 54, so that the air in the air tube 9a is sent into the water tube 9d. Thus, the water remaining in the water tube 9d is purged from the nozzle 11 at the distal end of the insert part 3.

It should be noted that the position of the air tube 9c may be shifted to the same level as the air tube 9a so that air is also sent into the air tube 9c when the apparatus is brought into a water purging state.

Figure 6:
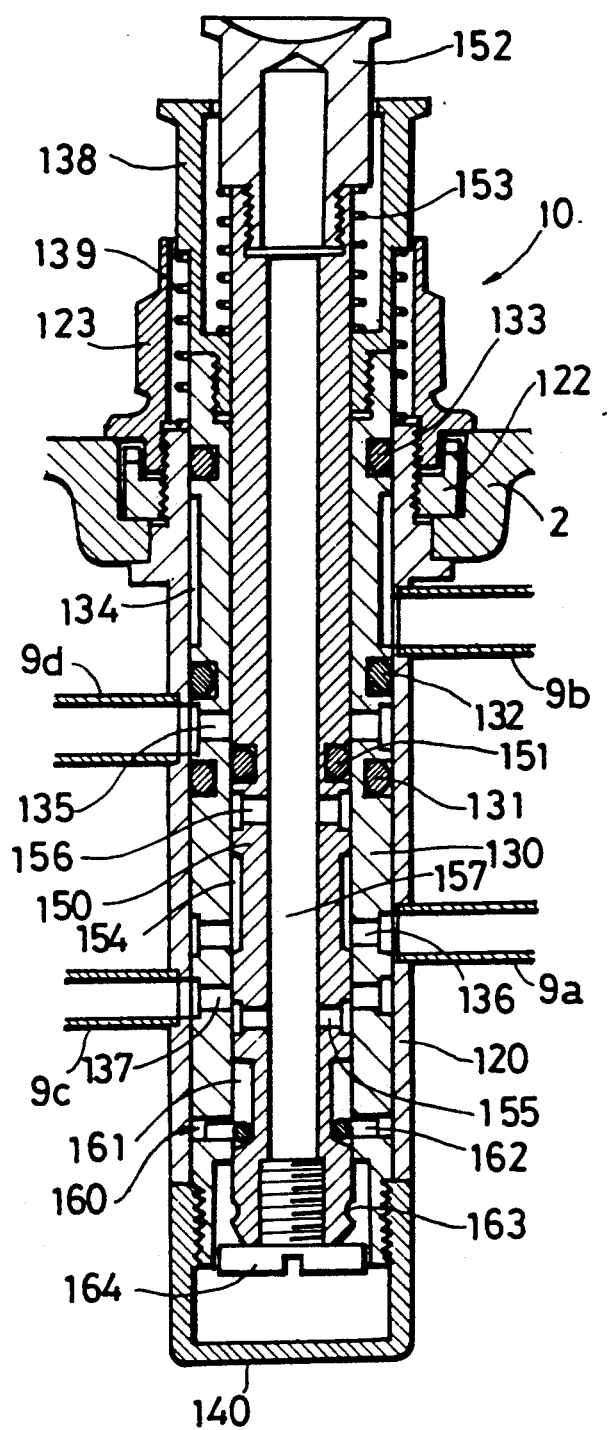
FIG. 6 is a sectional view of a second embodiment of the present invention in a stand-by state.

FIG. 6 shows the switching valve device 10 in the second embodiment of the present invention. In the figure, the reference numeral 120 denotes a cylinder. The air tube 9a, the water tube 9b, the air tube 9c and the water tube 9d are connected to respective portions of the side wall of the cylinder 120. The reference numeral 122 denotes a nut used to secure the cylinder 120 to the control part 2. The reference numeral 123 denotes a cylindrical cover member which surrounds the top portion of the cylinder 120.

Inside the cylinder 120 are provided a water supply switching valve body 130 for changing the condition of communication between the water tubes 9b and 9d and an air supply switching valve body 150 for changing the condition of communication between the air tubes 9a and 9c in such a manner that the two valve bodies 130 and 150 are slidable in the axial direction. The water supply switching valve body 130 is a cylindrical valve body which is fitted in the cylinder 120. The water supply switching valve body 130 has first to third O-rings 131, 132 and 133 fitted on the outer peripheral surface thereof. In a stand-by state, the first and second O-rings 131 and 132 seal the opening of the water tube 9d from both sides thereof, and the third O-ring 133 seals the area between the water supply switching valve body 130 and the inner wall of the cylinder 120 at a position above a communicating groove 134 for water which is formed above the second O-ring 132. In addition, a communicating hole 135 for purging is provided between the first and second O-rings 131 and 132, and communicating holes 136 and 137 for air are provided at respective positions which face the air tubes 9a and 9b, respectively.

The upper end (as viewed in the figure) of the water supply switching valve body 130 projects from the upper end of the cylinder 120. A water control button 138 is screwed onto the projecting end portion of the valve body 130. The water supply switching valve body 130 and the water control button 138 constitute in combination a water supply switching valve. The water supply switching valve body 130 is constantly biased in the direction in which it springs out of the cylinder 120 by a first coil spring 139 having relatively strong spring force. The reference numeral 140 denotes a bottom cover which covers the bottom of the water supply switching valve body 130 in such a manner that no water will leak, the cover 140 also serving as a stopper which prevents the water supply switching valve body 130 from coming off the cylinder 120 by abutting on the cylinder 120.

The air supply switching valve body 150 is slidably fitted in the water supply switching valve body 130, and an O-ring 151 for sealing is fitted on the fitting portion of the valve body 150. The upper end of the air supply switching valve body 150 projects from the upper end of the water supply switching valve body 130. An air control button 152 is screwed onto the projecting end portion of the air supply switching valve body 150, the air control button 152 projecting beyond the upper end of the water control button 138. The air supply switching valve body 150 and the air control button 152 constitute in combination an air supply switching valve. The reference numeral 153 denotes a second coil spring which biases the air supply switching valve body 150 in the direction in which it springs out of the water supply switching valve body 130, the second coil spring 153 being weaker than the first coil spring 139. It should be noted that the air supply switching valve body 150 in this embodiment is not provided with a leak hole for constantly leaking to the atmosphere the air sent into the cylinder 12 from the air tube 9a and it is hermetically closed with the air control button 152. Moreover, the air tube 9a is closed with the lower end portion of the air supply switching valve body 150. Therefore, there is no possibility that contaminative matter, for example, mucus or blood, in the patient's body cavity will flow backward into the cylinder 120 through the air tube 9c and there is no fear of such contaminative matter being scattered outside.

The reference numeral 154 denotes a communicating groove for air which serves as an air flow path when the apparatus is in an air supply state, and the reference numerals 155, 156 and 157 respectively denote communicating holes and passage for purging which serve as air flow paths when the apparatus is in a water purging state.

A click device 160 is provided in the area between the inner surface of the water supply switching valve body 130 and the outer surface of the air supply switching valve body 150. The click device 160 comprises a longitudinally elongated stroke limiting groove 161 formed in the outer periphery of the air supply switching valve body 150 and a click spring 162 which is inserted into the stroke limiting groove 161 from the water supply switching valve body side by means of spring force. The upper end surface of the stroke limiting groove 161 is formed into a flat surface, while the lower end surface is formed into a slant surface, so that, when abutting against the upper end surface of the stroke limiting groove 161, the click spring 162 cannot move over it, whereas, when abutting against the lower end surface of the stroke limiting groove 161, the click spring 62 can be moved out of the groove 161 if strong force is applied. The reference numeral 163 denotes a recess which engages with the click spring 162 when coming out of the stroke limiting groove 161. The reference numeral 164 denotes a stopper for preventing the air supply switching valve body 150 from coming off the water supply switching valve body 130, the stopper 164 being formed from a bolt which is screwed into the bottom of the air supply switching valve body 150.

The operation of the above-described embodiment will next be explained.

FIG. 6 shows the apparatus which is in a stand-by state. In this state, the air tubes 9a and 9c are cut off from each other by the air supply switching valve body 150, while the water tubes 9b and 9d are cut off from each other by the water supply switching valve body 130. Accordingly, neither air nor water is supplied.

Figure 7:
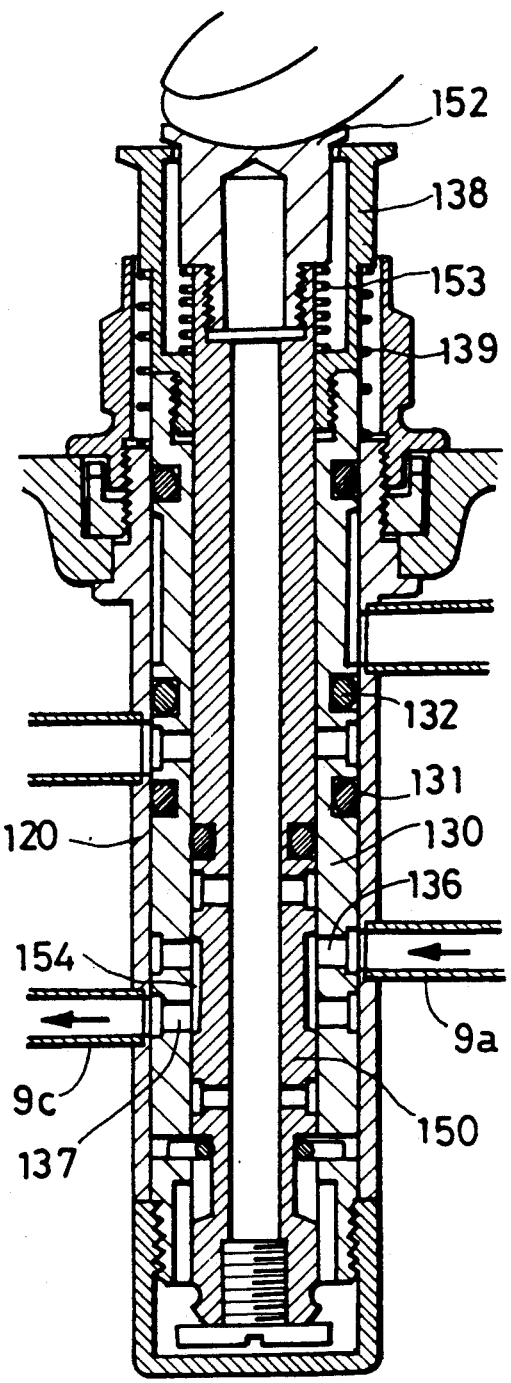
FIG. 7 is a sectional view of the second embodiment of the present invention in an air supply state.

When the air control button 152 is pressed down by a fingertip, as shown in FIG. 7, since the first coil spring 139 is stronger than the second coil spring 153, the water control button 138 is not pushed down, and the air control button 152 is alone pushed down. In consequence, the air supply switching valve body 150 is pushed into the water supply switching valve body 130. As a result, the air tubes 9a and 9c are communicated with each other through the communicating holes and groove 136, 137 and 154 for air and the air in the air tube 9a is sent into the air tube 9c, thus the apparatus entering into an air supply state.

Figure 8:
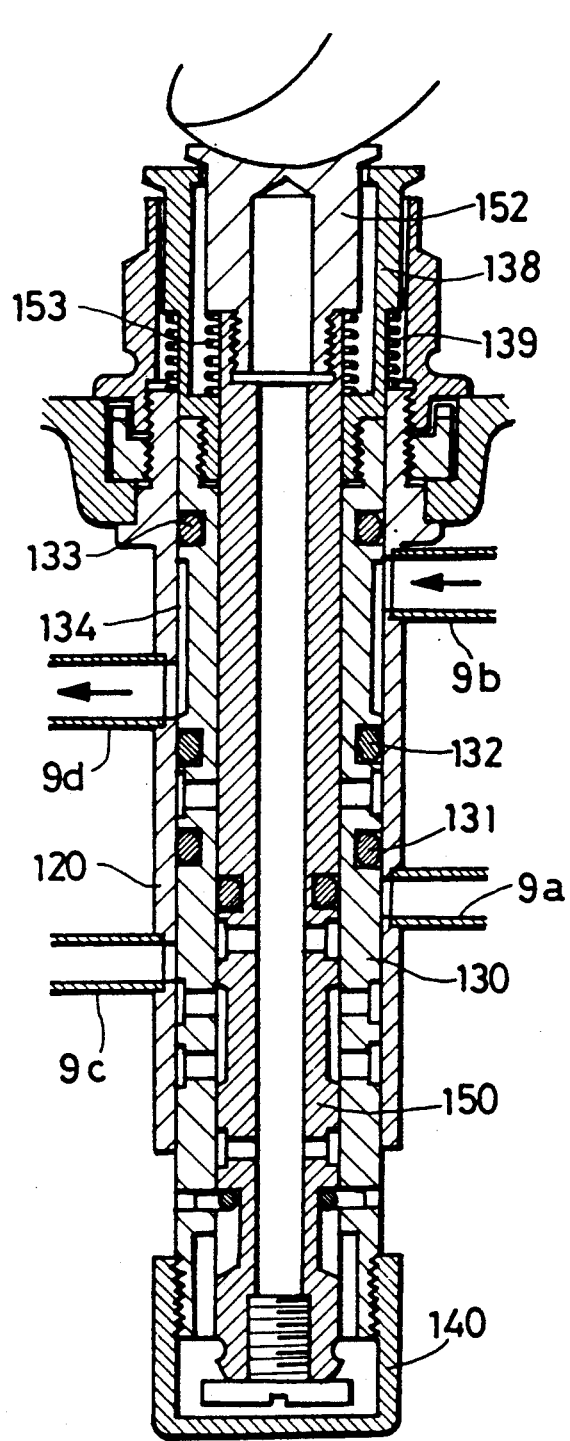
FIG. 8 is a sectional view of the second embodiment of the present invention in a water supply state.

As the air control button 152 is further pressed down by increasing the pressure thereon, as shown in FIG. 8, the first coil spring 139 is compressed and consequently the water control button 138 is pushed into the cylinder 120, together with the air control button 152. In consequence, the water supply switching valve body 130 is pushed into the cylinder 120. As a result, the air tubes 9a and 9c are cut off from each other by the water supply switching valve body 130. On the other hand, the water tubes 9b and 9d are communicated with each other through the communicating groove 134 for water, so that the water in the water tube 9b is sent into the water tube 9d, thus the apparatus entering into a water supply state.

Figure 9:
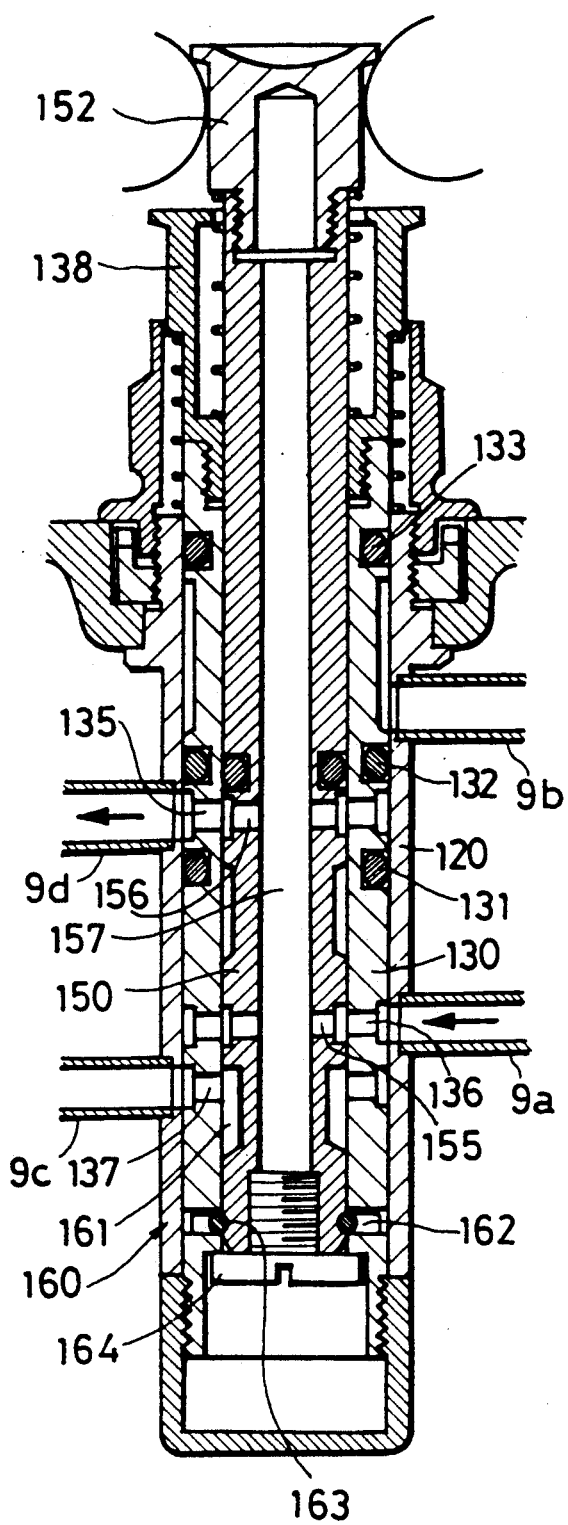
FIG. 9 is a sectional view of the second embodiment of the present invention in a state wherein the water remaining in the water tube is being purged.

When the air control button 152 that is in a stand-by position is pulled in the direction in which it is drawn out of the water control button 138, as shown in FIG. 9, the click spring 162 comes out of the stroke limiting groove 161 and engages with the recess 163, thus causing the air supply switching valve body 150 to move upward (as viewed in the figure). In consequence, the air and water tubes 9a and 9d are communicated with each other through the purging communicating holes and passage 135, 136, 155, 156 and 157 with the respective openings of the water and air tubes 9b and 9c being left closed, so that the air in the air tube 9a is sent into the water tube 9d. Thus, the water remaining in the water tube 9d is purged from the nozzle 11 at the distal end of the insert part 3.

It should be noted that the position of the air tube 9c may be shifted so that air is also sent into the air tube 9c when the apparatus is brought into a water purging state.

According to the present invention, the air in the air tube can be sent into the water tube to purge the water from the water tube simply by actuating the air and water supply switching valve device provided in the control part of the endoscope. Accordingly, after the endoscopic procedure of one patient has been completed, the water remaining in the water tube can be readily purged and discharged into the patient's body with the endoscope being left in the patient's body cavity. Thus, it is possible to completely eliminate the phenomenon that the water remaining in the water tube is scattered in the room and hence possible to prevent in-hospital infection. In addition, it is possible to release doctors from the problem that it is difficult to completely disinfect the inside of the thin water tube once contaminated even by use of ETO gas.

In regard to the arrangement of the apparatus, it suffices only to make a few improvements to an air and water supply switching valve device which has heretofore been employed and it is unnecessary to change the positional relationship and the water and air supply control operation. In addition, the water tank and other system constituent elements can be used as they are, and each of the switching valve bodies for air and water need not be provided with a key mechanism for preventing rotation. Thus, the apparatus of the present invention is simple and therefore can be readily realized.

While the invention has been described by reference to specific embodiments chosen for purposes of illustration, it should be apparent that numerous modifications could be made thereto by those skilled in the art without departing from the basic concept and scope of the invention.

What is claimed is:

1. An air and water supply apparatus for an endoscope having an elongated insert part and a control part connected to the proximal end of said insert part, comprising:
   a cylinder provided in said control part;
   a pair of first air and water tubes for supplying air and water, respectively, into said cylinder;
   a pair of second air and water tubes for sending air and water, respectively, to the distal end of said insert part from said cylinder;
   a water supply switching valve slidably provided in said cylinder to change the condition of communication between said first and second water tubes; and
   an air supply switching valve provided in said cylinder so as to be slidable in the same direction as the direction of slide of said water supply switching valve to change the condition of communication between said first and second air tubes,
   whereby said first air tube and said second water tube are communicated with each other by both said water and air supply switching valves sliding into said cylinder.

2. An air and water supply apparatus for an endoscope according to claim 1, wherein said water supply switching valve is slidably fitted in said cylinder, and said air supply switching valve is slidably fitted in said water supply switching valve.

3. An air and water supply apparatus for an endoscope having an elongated insert part and a control part connected to the proximal end of said insert part, comprising:
   a cylinder provided in said control part; and water, respectively, into said cylinder;
   a pair of second air and water tubes for sending air and water, respectively, to the distal end of said insert part from said cylinder;
   a water supply switching valve slidably provided in said cylinder to change the condition of communication between said first and second water tubes; and
   an air supply switching valve provided in said cylinder so as to be slidable in the same direction as the direction of slide of said water supply switching valve to change the condition of communication between said first and second air tubes,
   whereby in a stand-by state said first and second air and water tubes are cut off from each other by said air and water supply switching valves; when said air supply switching valve slides into said cylinder, said first and second air tubes are communicated with each other; when said water supply switching valve slides into said cylinder, together with said air supply switching valve, said first and second air tubes are cut off from each other, while said first and second water tubes are communicated with each other; and when both said water and air supply switching valves further slide into said cylinder, said first air tube and said second water tube are communicated with each other.

4. An air and water supply apparatus for an endoscope according to claim 3, wherein said water supply switching valve is slidably fitted in said cylinder, and said air supply switching valve is slidably fitted in said water supply switching valve.

5. An air and water supply apparatus for an endoscope according to claim 3, wherein in said stand-by state said air supply switching valve closes said first air tube.

6. An air and water supply apparatus for an endoscope according to claim 3, wherein in said stand-by state said air and water supply switching valves close all of said air and water tubes.

7. An air and water supply apparatus for an endoscope having an elongated insert part and a control part connected to the proximal end of said insert part, comprising:
   a cylinder provided in said control part;
   a pair of first air and water tubes for supplying air and water, respectively, into said cylinder;
   a pair of second air and water tubes for sending air and water, respectively, to the distal end of said insert part from said cylinder;
   a water supply switching valve slidably provided in said cylinder to change the condition of communication between said first and second water tubes; and
   an air supply switching valve provided in said cylinder so as to be slidable in the same direction as the direction of slide of said water supply switching valve to change the condition of communication between said first and second air tubes,
   whereby said first air tube and said second water tube are communicated with each other by said air supply switching valve sliding in the direction in which it is drawn out of said cylinder.

8. An air and water supply apparatus for an endoscope according to claim 7, wherein said water supply switching valve is slidably fitted in said cylinder, and said air supply switching valve is slidably fitted in said water supply switching valve.

9. An air and water supply apparatus for an endoscope having an elongated insert part and a control part connected to the proximal end of said insert part, comprising:
   a cylinder provided in said control part;
   a pair of first air and water tubes for supplying air and water, respectively, into said cylinder;
   a pair of second air and water tubes for sending air and water, respectively, to the distal end of said insert part from said cylinder;
   a water supply switching valve slidably provided in said cylinder to change the condition of communication between said first and second water tubes; and
   an air supply switching valve provided in said cylinder so as to be slidable in the same direction as the direction of slide of said water supply switching valve to change the condition of communication between said first and second air tubes,
   whereby in a stand-by state said first and second air and water tubes are cut off from each other by said air and water supply switching valves; when said air supply switching valve slides into said cylinder, said first and second air tubes are communicated with each other; when said water supply switching valve slides into said cylinder, together with said air supply switching valve, said first and second air tubes are cut off from each other, while said first and second water tubes are communicated with each other; and when said air supply switching valve which is in said stand-by state slides in the direction in which it is drawn out of said cylinder, said first air tube and said second water tube are communicated with each other.

10. An air and water supply apparatus for an endoscope according to claim 9, wherein in said stand-by state said air supply switching valve closes said first air tube.

11. An air and water supply apparatus for an endoscope according to claim 9, wherein in said stand-by state said air and water supply switching valves close all of said air and water tubes.

12. An air and water supply apparatus for an endoscope having an elongated insert part and a control part connected to the proximal end of said insert part, comprising:
- a cylinder provided in said control part;
- a pair of first air and water tubes for supplying air and water, respectively, into said cylinder;
- a pair of second air and water tubes for sending air and water, respectively, to the distal end of said insert part from said cylinder; and
- valve means provided in said cylinder, said valve means being capable of changing over at least the following two states from one to the other, that is, a state wherein said first and second water tubes are communicated with each other and a state wherein said first air tube and said second water tube are communicated with each other.

13. An air and water supply apparatus for an endoscope according to claim 12, wherein said valve means is slidably provided in said cylinder.

14. An air and water supply apparatus for an endoscope according to claim 12, wherein said valve means is capable of changing over the following three states from one to another, that is, a state wherein said first and second water tubes are communicated with each other, a state wherein said first and second air tubes are communicated with each other, and a state wherein said first air tube and said second water tube are communicated with each other.

15. An air and water supply apparatus for an endoscope according to claim 12, wherein said valve means is capable of changing over the following four states from one to another, that is, a state wherein neither of said first water and air tubes is communicated with said second water tube or said second air tube, a state wherein said first and second water tubes are communicated with each other, a state wherein said first and second air tubes are communicated with each other, and a state wherein said first air tube and said second water tube are communicated with each other.

* * * * *

UNITED STATES PATENT AND TRADEMARK OFFICE
CERTIFICATE OF CORRECTION

PATENT NO. : 5,027,791
DATED : July 2, 1991
INVENTOR(S) : N. TAKAHASHI

It is certified that error appears in the above-indentified patent and that said Letters Patent is hereby corrected as shown below:

Col. 9, line 41, after "part;" delete --and water,---.
Col. 9, line 42, before "respectively," insert --a a pair of first air and water tubes for supplying air and water,---.

Signed and Sealed this

Twelfth Day of April, 1994

Attest:

BRUCE LEHMAN

Attesting Officer

Commissioner of Patents and Trademarks